(12) United States Patent
Traina

(10) Patent No.: US 12,053,253 B2
(45) Date of Patent: Aug. 6, 2024

(54) ROBOTIC SURGICAL INSTRUMENT INCLUDING HIGH ARTICULATION WRIST ASSEMBLY WITH TORQUE TRANSMISSION AND MECHANICAL MANIPULATION

(71) Applicant: Covidien LP, Mansfield, MA (US)

(72) Inventor: Zachary Traina, Verona, NJ (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 18/449,892

(22) Filed: Aug. 15, 2023

(65) Prior Publication Data

US 2023/0380917 A1    Nov. 30, 2023

Related U.S. Application Data

(63) Continuation of application No. 16/769,938, filed as application No. PCT/US2019/012017 on Jan. 2, 2019, now Pat. No. 11,730,552.

(Continued)

(51) Int. Cl.
*A61B 34/00* (2016.01)
*A61B 17/072* (2006.01)
(Continued)

(52) U.S. Cl.
CPC ........ *A61B 34/35* (2016.02); *A61B 17/07207* (2013.01); *A61B 34/71* (2016.02);
(Continued)

(58) Field of Classification Search
None
See application file for complete search history.

(56) References Cited

U.S. PATENT DOCUMENTS

| 1,562,173 A | 11/1925 | Daniels |
| 2,777,340 A | 1/1957 | Hettwer et al. |

(Continued)

FOREIGN PATENT DOCUMENTS

| AU | 2008229795 A1 | 4/2009 |
| CA | 2451558 A1 | 1/2003 |

(Continued)

OTHER PUBLICATIONS

Extended European Search Report corresponding to EP No. 13 16 3033.7, completed Jun. 27, 2013 and dated Jul. 15. 2013.

(Continued)

*Primary Examiner* — Eyamindae C Jallow
(74) *Attorney, Agent, or Firm* — Carter, DeLuca & Farrell, LLP

(57) ABSTRACT

A robotic electromechanical surgical instrument includes a housing, an elongated shaft that extends distally from the housing, a wrist assembly supported on the elongated shaft, an end effector coupled to the wrist assembly, a universal joint assembly supported within the wrist assembly, and cables coupled to the wrist assembly. The elongated shaft defines a longitudinal axis. The wrist assembly includes a first joint coupled to a second joint. The universal joint assembly is rotatable to actuate a function of the end effector. The plurality of cables is movable to manipulate the first and second joints to enable the universal joint assembly and the wrist assembly to articulate relative to the longitudinal axis.

22 Claims, 14 Drawing Sheets

Related U.S. Application Data

(60) Provisional application No. 62/613,567, filed on Jan. 4, 2018.

(51) Int. Cl.
*A61B 34/35* (2016.01)
*A61B 17/00* (2006.01)
*A61B 17/29* (2006.01)
*A61B 34/30* (2016.01)

(52) U.S. Cl.
CPC ............. *A61B 2017/00367* (2013.01); *A61B 2017/00398* (2013.01); *A61B 2017/00477* (2013.01); *A61B 2017/0069* (2013.01); *A61B 2017/07257* (2013.01); *A61B 2017/07271* (2013.01); *A61B 2017/2927* (2013.01); *A61B 2034/305* (2016.02)

(56) References Cited

U.S. PATENT DOCUMENTS

| | | |
|---|---|---|
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,562,239 A | 10/1996 | Boiarski et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,135 A | 8/1998 | Madhani et al. |
| 5,797,900 A | 8/1998 | Madhani et al. |
| 5,807,377 A | 9/1998 | Madhani et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,976,122 A | 11/1999 | Madhani et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,364,888 B1 | 4/2002 | Niemeyer et al. |
| 6,368,324 B1 | 4/2002 | Dinger et al. |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,422,411 B1 | 7/2002 | Gray |
| 6,434,507 B1 | 8/2002 | Clayton et al. |
| 6,443,973 B1 | 9/2002 | Whitman |
| 6,460,718 B1 | 10/2002 | Vogel |
| 6,461,372 B1 | 10/2002 | Jensen et al. |
| 6,488,197 B1 | 12/2002 | Whitman |
| 6,491,201 B1 | 12/2002 | Whitman |
| 6,491,701 B2 | 12/2002 | Tierney et al. |
| 6,533,157 B1 | 3/2003 | Whitman |
| 6,537,280 B2 | 3/2003 | Dinger et al. |
| 6,554,844 B2 | 4/2003 | Lee et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,676,684 B1 | 1/2004 | Morley et al. |
| 6,685,698 B2 | 2/2004 | Morley et al. |
| 6,698,643 B2 | 3/2004 | Whitman |
| 6,699,177 B1 | 3/2004 | Wang et al. |
| 6,699,235 B2 | 3/2004 | Wallace et al. |
| 6,716,233 B1 | 4/2004 | Whitman |
| 6,746,443 B1 | 6/2004 | Morley et al. |
| 6,783,533 B2 | 8/2004 | Green et al. |
| 6,786,896 B1 | 9/2004 | Madhani et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,817,974 B2 | 11/2004 | Cooper et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,866,671 B2 | 3/2005 | Tierney et al. |
| 6,902,560 B1 | 6/2005 | Morley et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,066,926 B2 | 6/2006 | Wallace et al. |
| 7,077,856 B2 | 7/2006 | Whitman |
| 7,090,683 B2 | 8/2006 | Brock et al. |
| 7,111,769 B2 | 9/2006 | Wales et al. |

(56) References Cited

U.S. PATENT DOCUMENTS

| | | |
|---|---|---|
| 7,121,781 B2 | 10/2006 | Sanchez |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,169,141 B2 | 1/2007 | Brock et al. |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,297,142 B2 | 11/2007 | Brock |
| 7,316,681 B2 | 1/2008 | Madhani et al. |
| 7,320,700 B2 | 1/2008 | Cooper et al. |
| 7,328,828 B2 | 2/2008 | Ortiz et al. |
| 7,364,061 B2 | 4/2008 | Swayze et al. |
| 7,371,210 B2 | 5/2008 | Brock et al. |
| 7,380,695 B2 | 6/2008 | Doll et al. |
| 7,380,696 B2 | 6/2008 | Shelton, IV et al. |
| 7,398,707 B2 | 7/2008 | Morley et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,703,653 B2 | 4/2010 | Shah et al. |
| 7,721,931 B2 | 5/2010 | Shelton, IV et al. |
| 7,736,356 B2 | 6/2010 | Cooper et al. |
| 7,740,159 B2 | 6/2010 | Shelton, IV et al. |
| 7,743,960 B2 | 6/2010 | Whitman et al. |
| 7,744,608 B2 | 6/2010 | Lee et al. |
| 7,744,622 B2 | 6/2010 | Brock et al. |
| 7,758,569 B2 | 7/2010 | Brock |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,775,972 B2 | 8/2010 | Brock et al. |
| 7,780,651 B2 | 8/2010 | Madhani et al. |
| 7,789,875 B2 | 9/2010 | Brock et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,819,884 B2 | 10/2010 | Lee et al. |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,854,738 B2 | 12/2010 | Lee et al. |
| 7,857,185 B2 | 12/2010 | Swayze et al. |
| 7,862,580 B2 | 1/2011 | Cooper et al. |
| 7,867,241 B2 | 1/2011 | Brock et al. |
| 7,870,989 B2 | 1/2011 | Viola et al. |
| 7,890,211 B2 | 2/2011 | Green |
| 7,905,828 B2 | 3/2011 | Brock et al. |
| 7,905,897 B2 | 3/2011 | Whitman et al. |
| 7,914,522 B2 | 3/2011 | Morley et al. |
| 7,918,230 B2 | 4/2011 | Whitman et al. |
| 7,918,861 B2 | 4/2011 | Brock et al. |
| 7,922,719 B2 | 4/2011 | Ralph et al. |
| 7,942,868 B2 | 5/2011 | Cooper |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,004,229 B2 | 8/2011 | Nowlin et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,052,024 B2 | 11/2011 | Viola et al. |
| 8,056,787 B2 | 11/2011 | Boudreaux et al. |
| 8,083,667 B2 | 12/2011 | Cooper et al. |
| 8,105,320 B2 | 1/2012 | Manzo |
| 8,114,118 B2 | 2/2012 | Knodel et al. |
| 8,123,740 B2 | 2/2012 | Madhani et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,160,743 B2 | 4/2012 | Birkenbach et al. |
| 8,182,470 B2 | 5/2012 | Devengenzo et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,292,916 B2 | 10/2012 | Grace |
| 8,303,581 B2 | 11/2012 | Arts et al. |
| 8,337,521 B2 | 12/2012 | Cooper et al. |
| 8,342,379 B2 | 1/2013 | Whitman et al. |
| 8,343,141 B2 | 1/2013 | Madhani et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,398,634 B2 | 3/2013 | Manzo et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,967,443 B2 | 3/2015 | McCuen |
| 9,161,771 B2 * | 10/2015 | Steger .................. A61B 17/29 |
| 9,295,522 B2 | 3/2016 | Kostrzewski |
| 11,203,114 B2 * | 12/2021 | Kikuchi .................. B25J 9/06 |
| 11,730,552 B2 | 8/2023 | Traina |
| 2003/0038938 A1 | 2/2003 | Jung et al. |
| 2004/0111012 A1 | 6/2004 | Whitman |

(56) References Cited

U.S. PATENT DOCUMENTS

| | | |
|---|---|---|
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0027467 A1 | 2/2006 | Ferguson |
| 2006/0142656 A1 | 6/2006 | Malackowski et al. |
| 2006/0199999 A1* | 9/2006 | Ikeda ............... A61B 1/00149 600/141 |
| 2006/0278680 A1 | 12/2006 | Viola |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0287963 A1* | 11/2008 | Rogers ............... A61B 1/009 606/130 |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0112316 A1* | 4/2009 | Umemoto ............. A61B 34/71 700/258 |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0160735 A1* | 6/2010 | Bakos ............... A61B 34/71 600/141 |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0077673 A1 | 3/2011 | Grubac et al. |
| 2011/0118707 A1 | 5/2011 | Burbank |
| 2011/0118708 A1 | 5/2011 | Burbank et al. |
| 2011/0118709 A1 | 5/2011 | Burbank |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0089131 A1 | 4/2012 | Zemlok et al. |
| 2012/0143002 A1 | 6/2012 | Aranyi et al. |
| 2012/0172924 A1 | 7/2012 | Allen, IV |
| 2012/0209253 A1* | 8/2012 | Donhowe ............ A61B 17/00 606/1 |
| 2012/0223121 A1 | 9/2012 | Viola et al. |
| 2012/0253326 A1 | 10/2012 | Kleyman |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2013/0018361 A1 | 1/2013 | Bryant |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0188159 A1 | 7/2014 | Steege |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0272582 A1 | 10/2015 | Leimbach et al. |
| 2015/0297199 A1 | 10/2015 | Nicholas et al. |
| 2016/0066937 A1 | 3/2016 | Steger |
| 2016/0242779 A1 | 8/2016 | Aranyi et al. |
| 2016/0296216 A1 | 10/2016 | Nicholas et al. |
| 2017/0056118 A1* | 3/2017 | Cooper ............... A61B 34/30 |
| 2017/0095922 A1* | 4/2017 | Licht ................. A61B 34/71 |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1813212 A1 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |

(56) References Cited

FOREIGN PATENT DOCUMENTS

| | | | |
|---|---|---|---|
| EP | 2165664 | A2 | 3/2010 |
| EP | 2236098 | A2 | 10/2010 |
| EP | 2245994 | A1 | 11/2010 |
| EP | 2263568 | A2 | 12/2010 |
| EP | 2272443 | A1 | 1/2011 |
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2377472 | A1 | 10/2011 |
| EP | 2462878 | A1 | 6/2012 |
| EP | 2462880 | A2 | 6/2012 |
| EP | 2491872 | A1 | 8/2012 |
| EP | 2586382 | A2 | 5/2013 |
| EP | 2606834 | A2 | 6/2013 |
| EP | 2676615 | A2 | 12/2013 |
| EP | 2815705 | A1 | 12/2014 |
| EP | 3192455 | A1 | 7/2017 |
| EP | 3369384 | A2 | 9/2018 |
| ES | 2333509 | A1 | 2/2010 |
| FR | 2861574 | A1 | 5/2005 |
| JP | 08038488 | | 2/1996 |
| JP | 2005125075 | A | 5/2005 |
| WO | 9915086 | A1 | 4/1999 |
| WO | 0072760 | A1 | 12/2000 |
| WO | 0072765 | A1 | 12/2000 |
| WO | 03000138 | A2 | 1/2003 |
| WO | 03026511 | A1 | 4/2003 |
| WO | 03030743 | A2 | 4/2003 |
| WO | 03065916 | A1 | 8/2003 |
| WO | 03077769 | A1 | 9/2003 |
| WO | 03090630 | A3 | 4/2004 |
| WO | 2004107989 | A1 | 12/2004 |
| WO | 2006042210 | A2 | 4/2006 |
| WO | 2007014355 | A2 | 2/2007 |
| WO | 2007016290 | A2 | 2/2007 |
| WO | 2007026354 | A1 | 3/2007 |
| WO | 2007137304 | A2 | 11/2007 |
| WO | 2008131362 | A2 | 10/2008 |
| WO | 2008133956 | A2 | 11/2008 |
| WO | 2009039506 | A1 | 3/2009 |
| WO | 2009132359 | A2 | 10/2009 |
| WO | 2009143092 | A1 | 11/2009 |
| WO | 2009149234 | A1 | 12/2009 |
| WO | 2011060315 | A2 | 5/2011 |
| WO | 2011108840 | A2 | 9/2011 |
| WO | 2012040984 | A1 | 4/2012 |
| WO | 2017053358 | A1 | 3/2017 |
| WO | 2017083125 | A1 | 5/2017 |
| WO | 2018049211 | A1 | 3/2018 |

OTHER PUBLICATIONS

Extended European Search Report corresponding to EP No. 11 17 8021.9, dated Jun. 4, 2013.
Extended European Search Report corresponding to EP No. 12 18 6177.7, completed Aug. 14, 2013 and dated Aug. 23, 2013.
Partial European Search Report corresponding to EP No. 13 17 2400.7, completed Sep. 18, 2013 and dated Oct. 1, 2013.
Partial European Search Report corresponding to EP No. 13 17 1742.3, completed Sep. 17, 2013 and dated Sep. 25, 2013.
Extended European Search Report corresponding to EP No. 13 17 5475.6, completed Sep. 23, 2013 and dated Oct. 1, 2013.
Extended European Search Report corresponding to EP No. 13 17 5478.0, completed Sep. 24, 2013 and dated Oct. 2, 2013.
Extended European Search Report corresponding to EP No. 08 25 27037, completed Oct. 23, 2008 and dated Oct. 31, 2008.
International Search Report from the corresponding EP Application No. 12186177.7 dated Aug. 23, 2013.
International Search Report corresponding to PCT/US2005/027266, completed May 30, 2008 and dated Jun. 18, 2008.
Extended European Search Report corresponding to EP 08 25 3184.9, completed Feb. 12, 2009 and dated Feb. 27, 2009.
Extended European Search Report corresponding to EP 10 25 0228.3, completed May 20, 2010 and dated Jun. 1, 2010.
Extended European Search Report corresponding to EP 10 25 2037.6, completed Mar. 1, 2011 and dated Mar. 9, 2011.
Extended European Search Report corresponding to EP 10 25 1968.3, completed on Jul. 4, 2011 and dated Jul. 14, 2011.
Extended European Search Report corresponding to EP 11 15 2266.0, completed Jul. 15, 2011 and dated Jul. 28, 2011.
Extended European Search Report corresponding to EP 11 25 0462.6, completed Jul. 20, 2011 and dated Jul. 28, 2011.
Extended European Search Report corresponding to EP 11 25 0771.0, completed Feb. 7, 2012 and dated Feb. 17, 2012.
Extended European Search Report corresponding to EP 06 78 8914.7, completed May 3, 2012 and dated May 11, 2012.
Partial European Search Report corresponding to EP 12 18 6177.7, completed Jan. 30, 2013 and dated Feb. 12, 2013.
Extended European Search Report corresponding to EP 08 25 2703.7, completed Oct. 23, 2008 and dated Oct. 31, 2008.
European Search Report No. 14192217.9 dated Feb. 5, 2015.
Extended European Search Report corresponding to EP No. 13 17 5479.8, completed Sep. 27, 2013 and dated Oct. 10, 2013.
Partial Extended European Search Report corresponding to EP 13 17 5477.2, completed Oct. 7, 2013 and dated Oct. 15, 2013.
European search Report from Appl. No. 13177163.6 dated Nov. 15, 2013.
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
India Examination Report for application No. 202017026814 dated Dec. 8, 2022 with English translation.
Chinese Office Action for Application No. 2019800073840 dated Feb. 22, 2023 with English Translation.
Japanese Office Action for Application No. 2020-537012 dated Jun. 18, 2021 with English Translation.
Extended European Search Report for U.S. Appl. No. 19/735,721 dated Dec. 13, 2021.

\* cited by examiner

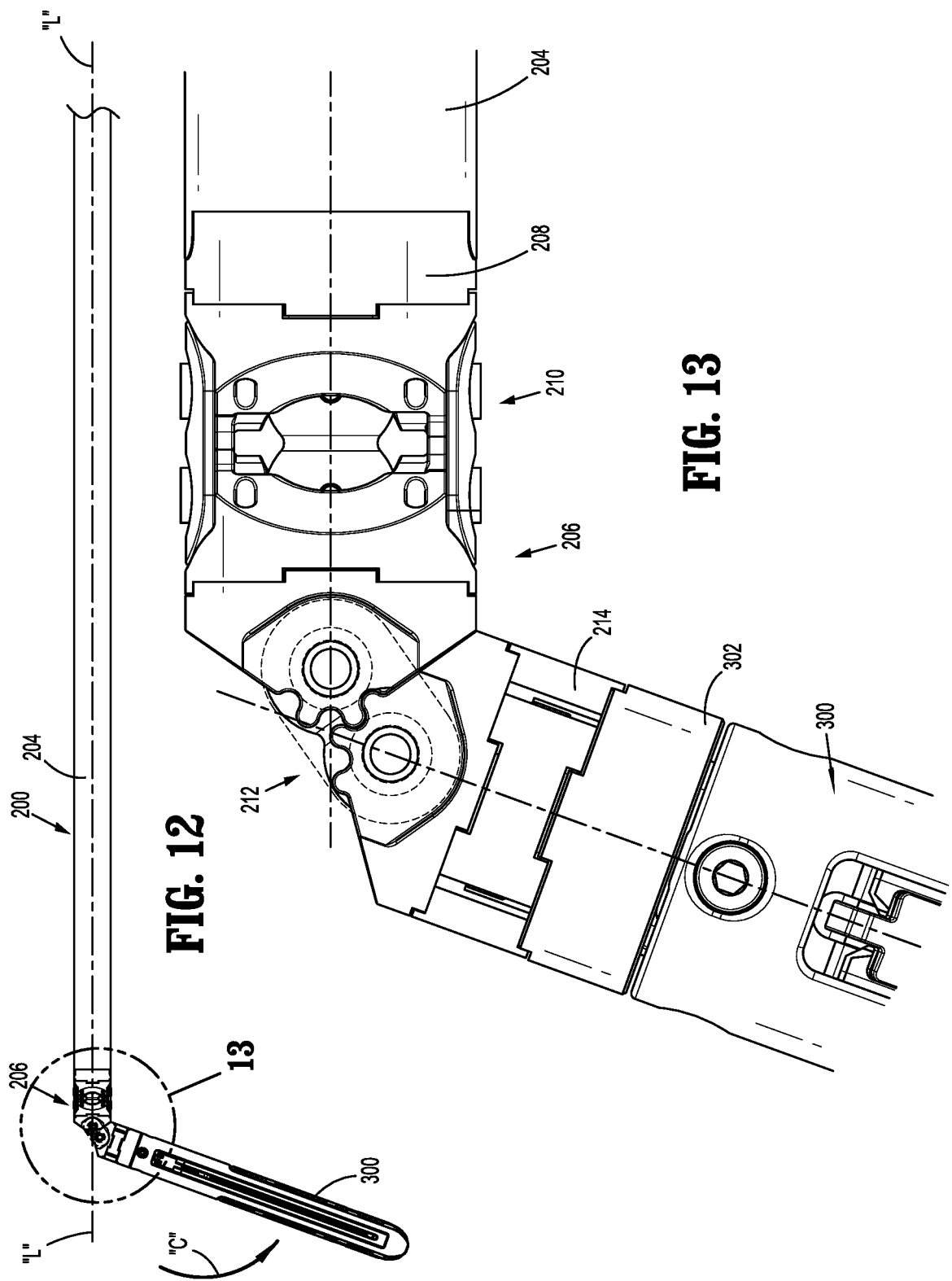

ROBOTIC SURGICAL INSTRUMENT INCLUDING HIGH ARTICULATION WRIST ASSEMBLY WITH TORQUE TRANSMISSION AND MECHANICAL MANIPULATION

CROSS-REFERENCE TO RELATED APPLICATIONS

This application is a Continuation Application which claims the benefit of and priority to U.S. patent application Ser. No. 16/769,938, filed Jun. 4, 2020, which is a U.S. National Stage Application filed under 35 U.S.C. § 371(a) of International Patent Application Serial No. PCT/US2019/012017, filed Jan. 2, 2019, which claims the benefit of and priority to U.S. Provisional Patent Application Ser. No. 62/613,567, filed Jan. 4, 2018, the entire disclosure of which is incorporated by reference herein.

BACKGROUND

Robotic surgical systems have been used in minimally invasive medical procedures. Some robotic surgical systems include a console supporting a surgical robotic arm and a surgical instrument having at least one end effector (e.g., a forceps or a stapling device) mounted to the robotic arm. The robotic arm provides mechanical power to the surgical instrument for its operation and movement. Each robotic arm may include an instrument drive unit that is operatively connected to the surgical instrument. The surgical instruments may include cables that are motor driven to operate end effectors of the surgical instruments.

SUMMARY

The present disclosure relates to surgical instruments for use in surgical procedures. More specifically, the present disclosure relates to articulable robotic surgical instruments for robotic surgical systems used to conduct minimally invasive surgical procedures. The present disclosure provides for smaller surgical instruments for robotic surgical systems that provide increased articulation, torque transmission, and mechanical manipulation.

In accordance with an aspect of the present disclosure, a robotic electromechanical surgical instrument is provided. The surgical instrument includes a housing, an elongated shaft that extends distally from the housing, a wrist assembly supported on the elongated shaft, an end effector coupled to the wrist assembly, a universal joint assembly supported within the wrist assembly, and cables coupled to the wrist assembly.

The elongated shaft defines a longitudinal axis. The wrist assembly includes a first joint coupled to a second joint. The universal joint is rotatable to actuate a function of the end effector. The cables are movable to manipulate the first and second joints to enable the universal joint assembly and the wrist assembly to articulate relative to the longitudinal axis.

In some embodiments, the first and second joints may be angularly displaced relative to one another about the longitudinal axis.

In certain embodiments, each of the first and second joints may have a proximal segment and a distal segment. The proximal and distal segments may be supported for movement relative to one another to facilitate articulation of the wrist assembly relative to the longitudinal axis of the elongated shaft. The proximal and distal segments of the first joint may include couplers (e.g., gears) supported in rolling contact with one another. The proximal and distal segments of the second joint may include couplers (e.g., gears) supported in rolling contact with one another. The proximal and distal segments of the first joint may be coupled together by a first pair of links and the proximal and distal segments of the second joint may be coupled together by a second pair of links.

Further, although various gears/couplers are described herein, such gears/couplers may include couplers, gears, gear-like geometry, other suitable interleaving geometry, and/or combinations thereof. For instance, such gears/couplers may be configured to enforce deterministic rolling motion of one portion of a joint over another portion of the joint and/or may otherwise be configured for high-friction engagement.

In some embodiments, the first joint of the wrist assembly may be coupled to the elongated shaft by a first tubular interface and the second joint of the wrist assembly may be coupled to the end effector by a second tubular interface. The first joint may be rotationally locked to the first tubular interface and the second joint may be rotationally locked to the second tubular interface.

In certain embodiments, the first and second joints may define central openings therethrough that are positioned to receive the universal joint assembly therein.

In certain embodiments, the universal joint assembly may include two or more universal joints positioned at longitudinally spaced apart locations along the universal joint assembly.

According to another aspect, a robotic surgical system is provided. The robotic surgical system includes a robotic surgical assembly and an electromechanical surgical instrument selectively mounted to the robotic surgical assembly.

The surgical instrument includes a housing, an elongated shaft that extends distally from the housing to a wrist assembly, a firing assembly that extends through the wrist assembly and includes universal joints, an end effector supported on the wrist assembly and secured to the firing assembly, and a cable drive assembly.

The elongated shaft defines a longitudinal axis. The wrist assembly includes a first joint coupled to a second joint. The cable drive assembly is actuatable by the robotic surgical assembly to manipulate the first and second joints and enable the firing assembly and the wrist assembly to articulate relative to the longitudinal axis.

In some embodiments, the first and second joints are angularly displaced relative to one another about the longitudinal axis. Each of the first and second joints may have a proximal segment and a distal segment. The proximal and distal segments may be supported for movement relative to one another to facilitate articulation of the wrist assembly relative to the longitudinal axis of the elongated shaft. The proximal and distal segments of the first joint may include couplers (e.g., gears) supported in rolling contact with one another. The proximal and distal segments of the second joint may include couplers (e.g., gears) supported in rolling contact with one another.

The proximal and distal segments of the first joint may be coupled together by a first pair of links and the proximal and distal segments of the second joint may be coupled together by a second pair of links.

In some embodiments, the first joint of the wrist assembly may be coupled to the elongated shaft by a first tubular interface and the second joint of the wrist assembly may be coupled to the end effector by a second tubular interface. The first joint may be rotationally locked to the first tubular interface and the second joint may be rotationally locked to the second tubular interface.

In certain embodiments, the first and second joints may define central openings therethrough that are positioned to receive the firing assembly therein.

In some embodiments, two or more universal joints may be positioned at longitudinally spaced apart locations along the firing assembly.

Advantageously, the presently disclosed surgical instruments provide deterministic end effector position while resisting external loading (e.g., from the patient anatomy) from affecting the drive system. In addition, the presently disclosed surgical instruments include knuckle gearing (or coupling) with interlocking geometry that maintains rolling contact between gears to prevent 'S' condition in the joint where the end effector location would be non-deterministic.

The presently disclosed surgical instruments also provide high articulation (e.g. +/−70 degrees) in two directions while maintaining minimal bend radius. In some embodiments, additional cables can be routed to provide additional mechanical functionality at the end effector (e.g., a dedicated grasp function).

Other aspects, features, and advantages provided by some or all of the illustrative embodiments described herein will be apparent from the description, the drawings, and the claims that follow.

BRIEF DESCRIPTION OF THE DRAWINGS

The accompanying drawings, which are incorporated in and constitute a part of this specification, illustrate embodiments of the present surgical instruments for robotic surgical systems and, together with a general description of the disclosure given above, and the detailed description of the embodiment(s) given below, serve to explain the principles of the disclosure, wherein:

FIG. 12 is a top view of a distal portion of the surgical instrument of FIG. 2 with the wrist assembly thereof shown in an articulated position;

FIG. 13 is an enlarged view of the indicated area of detail shown in FIG. 12;

DETAILED DESCRIPTION

Figure 1:
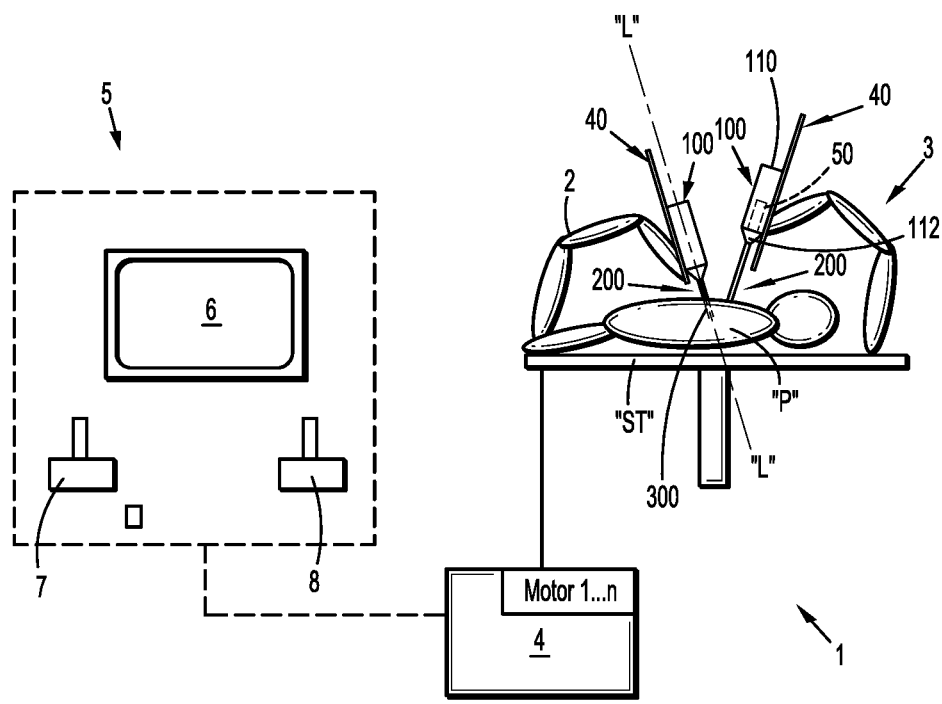
FIG. 1 is a schematic illustration of a robotic surgical system in accordance with the present disclosure.

Embodiments of the present surgical instruments for robotic surgical systems are described in detail with reference to the drawings, in which like reference numerals designate identical or corresponding elements in each of the several views. As used herein, the term "distal" refers to structure that is closer to a patient, while the term "proximal" refers to structure farther from the patient.

As used herein, the term "clinician" refers to a doctor, nurse, or other care provider and may include support personnel. In the following description, well-known functions or constructions are not described in detail to avoid obscuring the present disclosure in unnecessary detail.

Referring initially to FIG. 1, a surgical system, such as, for example, a robotic surgical system 1, generally includes one or more surgical robotic arms 2, 3, a control device 4, and an operating console 5 coupled with control device 4. Any of the surgical robotic arms 2, 3 may have a robotic surgical assembly 100 and an electromechanical surgical instrument 200 coupled thereto. Electromechanical surgical instrument 200 includes an end effector 300 disposed at a distal portion thereof. In some embodiments, robotic surgical assembly 100 may be removably attached to a slide rail 40 of one or more of surgical robotic arms 2, 3. In certain embodiments, robotic surgical assembly 100 may be fixedly attached to slide rail 40 of one or more of surgical robotic arms 2, 3.

Operating console 5 of robotic surgical system 1 includes a display device 6, which is set up to display three-dimensional images; and manual input devices 7, 8, by means of which a clinician (not shown), is able to telemanipulate the robotic arms 2, 3 of robotic surgical system 1 in a first operating mode, as known in principle to a person skilled in the art. Each robotic arm of robotic arms 2, 3 may be composed of any number of members, which may be connected through any number of joints. Robotic arms 2, 3 may be driven by electric drives (not shown) that are connected to control device 4. Control device 4 (e.g., a computer) of robotic surgical system 1 is set up to activate the drives, for example, by means of a computer program, in such a way that robotic arms 2, 3, the attached robotic surgical assembly 100, and thus electromechanical surgical instrument 200 (including end effector 300) of robotic surgical system 1 execute a desired movement according to a movement defined by means of manual input devices 7, 8. Control device 4 may be set up in such a way that it regulates movement of robotic arms 2, 3 and/or of the drives.

Robotic surgical system 1 is configured for use on a patient "P" positioned (e.g., lying) on a surgical table "ST" to be treated in a minimally invasive manner by means of a surgical instrument, e.g., electromechanical surgical instrument 200 and, more specifically, end effector 300 of electromechanical surgical instrument 200. Robotic surgical system 1 may include more than two robotic arms 2, 3, the additional robotic arms are likewise connected to control device 4 and telemanipulatable by means of operating console 5. A surgical instrument, for example, electromechanical surgical instrument 200 (including end effector 300 thereof), may also be attached to any additional robotic arm(s).

Control device 4 of robotic surgical system 1 may control one or more motors (not shown), each motor configured to drive movement of robotic arms 2, 3 in any number of directions. Control device 4 may control an instrument drive unit 110 including one or more motors 50 (or motor packs). Motors 50 drive various operations of end effector 300 of electromechanical surgical instrument 200. Motors 50 may include a rotation motor, such as, for example, a canister motor. One or more of motors 50 (or a different motor, not shown) may be configured to drive a rotation of electromechanical surgical instrument 200, or components thereof, relative to a longitudinal axis "L-L" thereof. The one or more motors can be configured to effect operation and/or movement of electromechanical end effector 300 of electromechanical surgical instrument 200.

Figure 2:
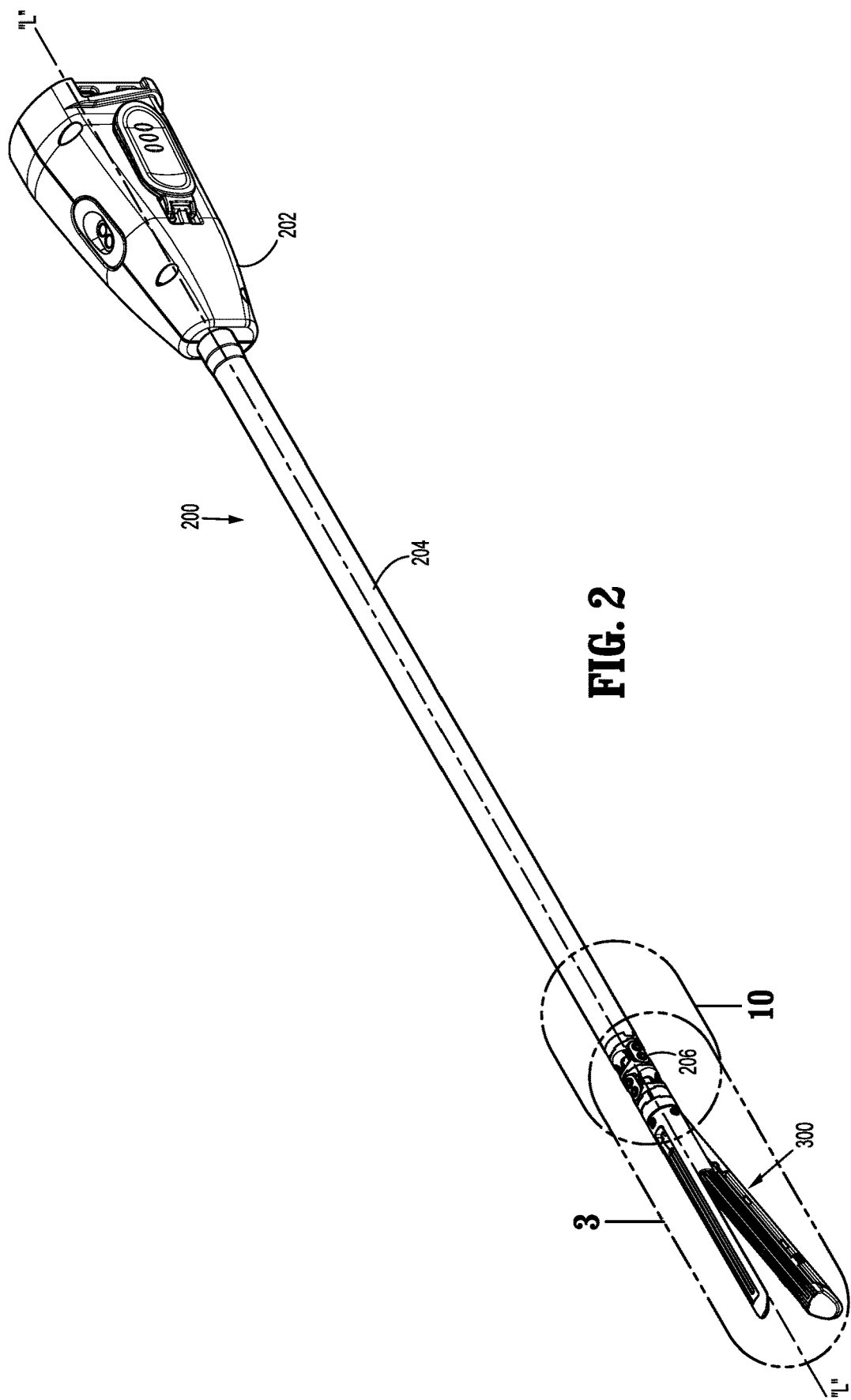
FIG. 2 is a perspective view of a surgical instrument of the robotic surgical system of FIG. 1 in an unarticulated position.

Turning now to FIG. 2, electromechanical surgical instrument 200 of robotic surgical system 1 includes a housing 202 at a proximal end portion thereof and an elongated shaft 204 that extends distally from housing 202. Elongated shaft 204 includes a wrist assembly 206 supported on a distal end portion of elongated shaft 204 that couples end effector 300 to elongated shaft 204.

Housing 202 of electromechanical surgical instrument 200 is configured to selectively couple to instrument drive unit 110 of robotic surgical assembly 100, for example, via side loading on a sterile interface module 112 of robotic surgical assembly 100, to enable motors of instrument drive unit 110 of robotic surgical assembly 100 to operate end effector 300 of electromechanical surgical instrument 200. Housing 202 of electromechanical surgical instrument 200 supports a drive assembly 203 that mechanically and/or electrically cooperates with motors of instrument drive unit 110 of robotic surgical assembly 100.

Figure 3:
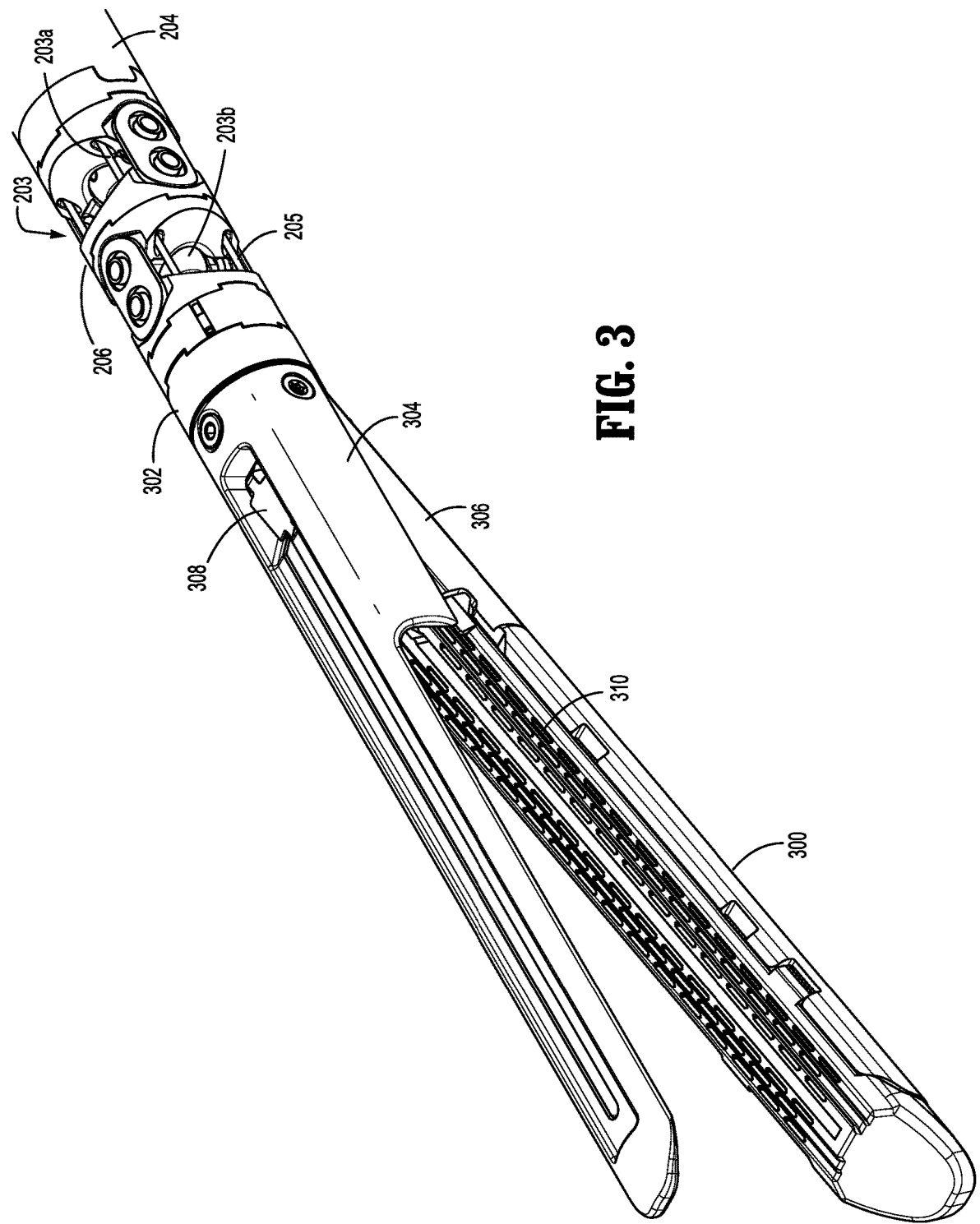
FIG. 3 is an enlarged, perspective view of the indicated area of detail shown in FIG. 2.
Figure 4:
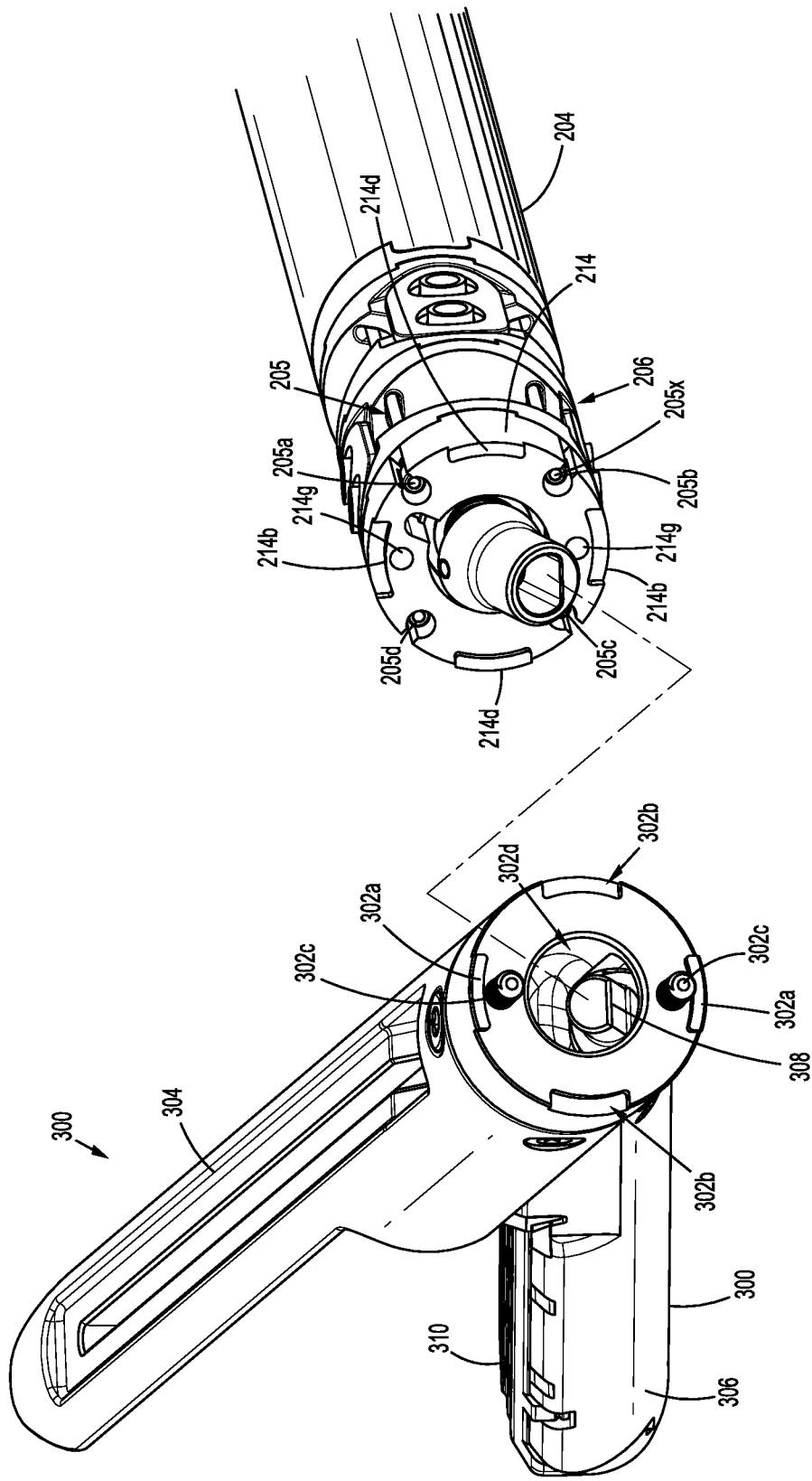
FIG. 4 is a perspective view of an end effector of the surgical instrument of FIG. 2 shown separated from a wrist assembly of an elongated shaft assembly of the surgical instrument.

Drive assembly 203 of electromechanical surgical instrument 200 can include any suitable electrical and/or mechanical component to effectuate driving force/movement, and which components may be similar to components of the drive assembly described in commonly owned International Application Publication No. WO2017053358, filed Sep. 21, 2016, the entire disclosure of which is incorporated by reference herein. In particular, as seen in FIGS. 3 and 4, drive assembly 203 of electromechanical surgical instrument 200 includes a cable drive assembly 203a and a firing assembly 203b. The cable drive assembly 203a is similar to that described in commonly owned U.S. Patent Application Publication No. 2015/0297199, filed Oct. 22, 2015 and entitled "Adapter Assembly with Gimbal for Interconnecting Electromechanical Surgical Devices and Surgical Loading Units, and Surgical Systems Thereof," the entire disclosure of which is incorporated by reference herein.

Figure 15:
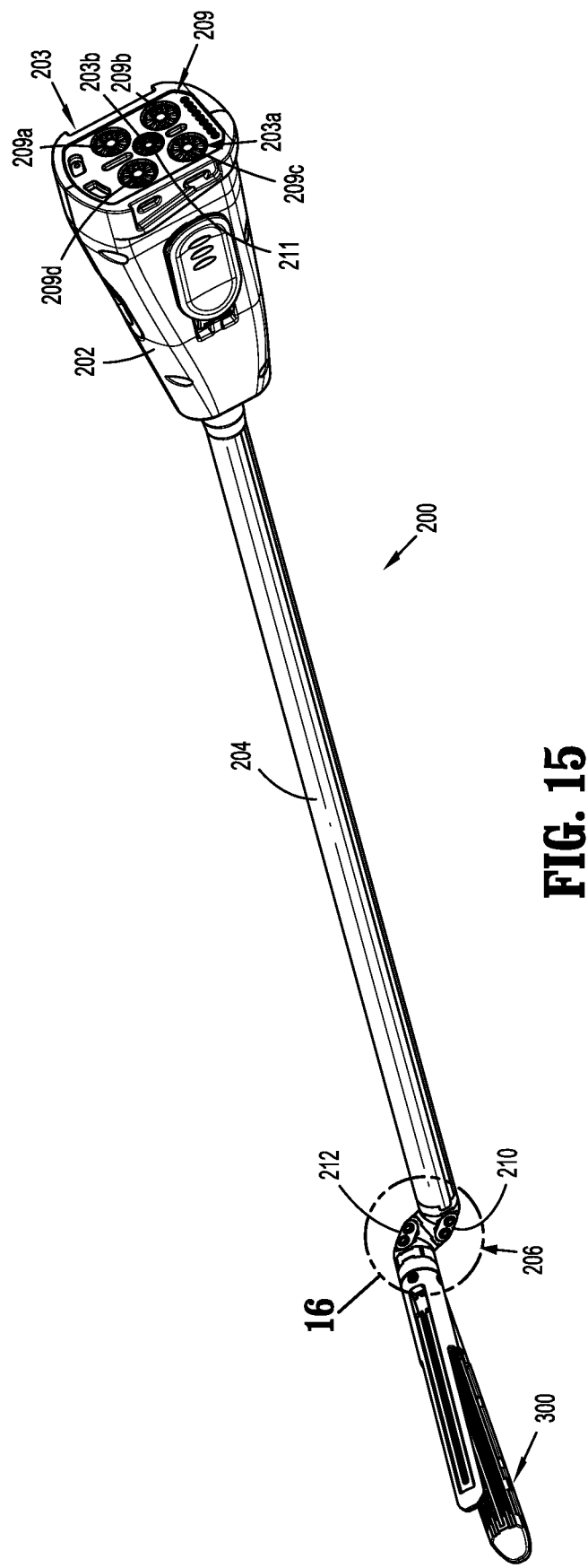
FIG. 15 is a perspective view of the surgical instrument of FIG. 2 shown in an exemplary articulated position.

With reference to FIGS. 1 and 15, cable drive assembly 203a of electromechanical surgical instrument 200 includes one or more driven members 209, such as driven members 209a, 209b, 209c, 209d (FIG. 15), to enable robotic surgical assembly 100 to transfer power and actuation forces from motors 50 of robotic surgical assembly 100 to ultimately drive movement of components of end effector 300 of electromechanical surgical instrument 200.

As seen in FIGS. 3 and 4, cable drive assembly 203a of electromechanical surgical instrument 200 includes cables 205, such as cables 205a, 205b, 205c, and 205d, which are coupled to a respective driven member 209a, 209b, 209c, 209d (FIG. 15) of electromechanical surgical instrument 200 at a proximal end portion thereof. Cables 205 of cable drive assembly 203a extend distally to distal end portions thereof, and may include ferrules 205x (FIG. 4) that couple to wrist assembly 206 of elongated shaft 204 at circumferentially spaced apart locations (e.g., angularly displaced) about the longitudinal axis "L-L" to enable cables 205 to effectuate an articulation/rotation/pitch/yaw of wrist assembly 206 of electromechanical surgical instrument 200 and end effector 300 of electromechanical surgical instrument 200 upon actuation of one or more of cables 205. Cable drive assembly 203a can include one or more pulleys, friction wheels, gears, couplers, rack and pinion arrangements, etc. coupled directly or indirectly to driven members 209 and/or cables 205 to facilitate driving movement imparted through driven members 209 and/or cables 205. The cables 205 can be arranged such that diagonal cables (e.g. cables 205d, 205b or cables 205a, 205c; see FIG. 4) can be positioned to be driven in opposite directions in order to provide articulation in multiple axes (e.g. two). Although only four cables are shown, cable drive assembly 203a can include any number of cables, for example, to provide additional functionally at the end effector 300.

Figure 5:
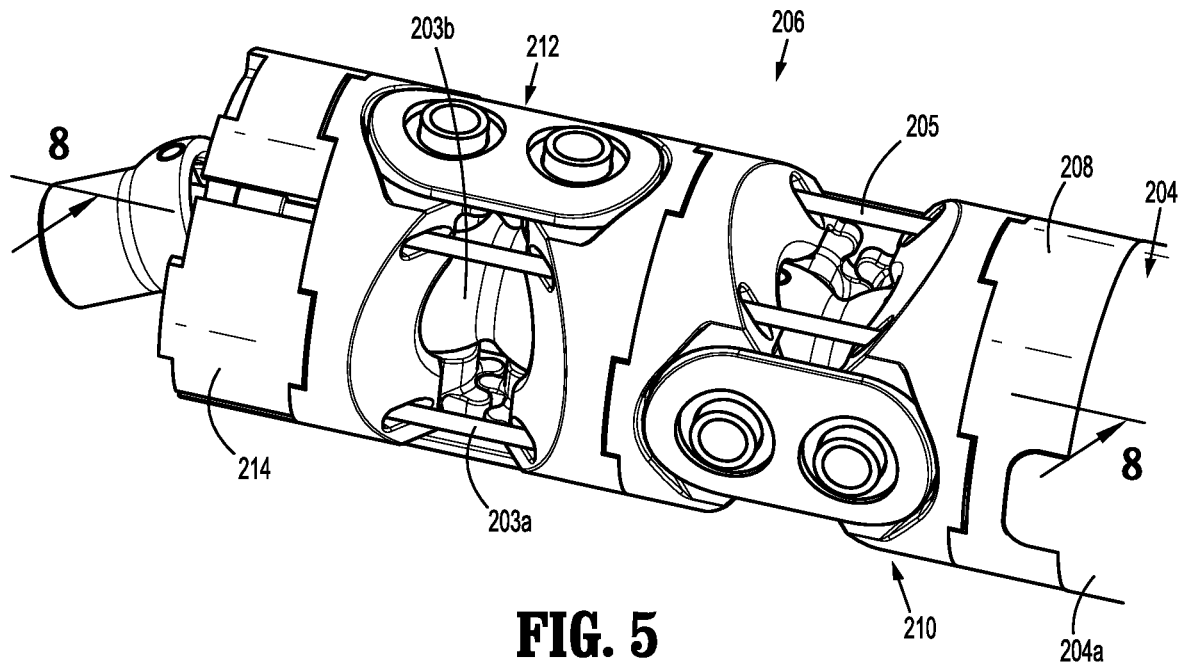
FIGS. 5 and 6 are perspective views of the wrist assembly of FIG. 4.
Figure 6:
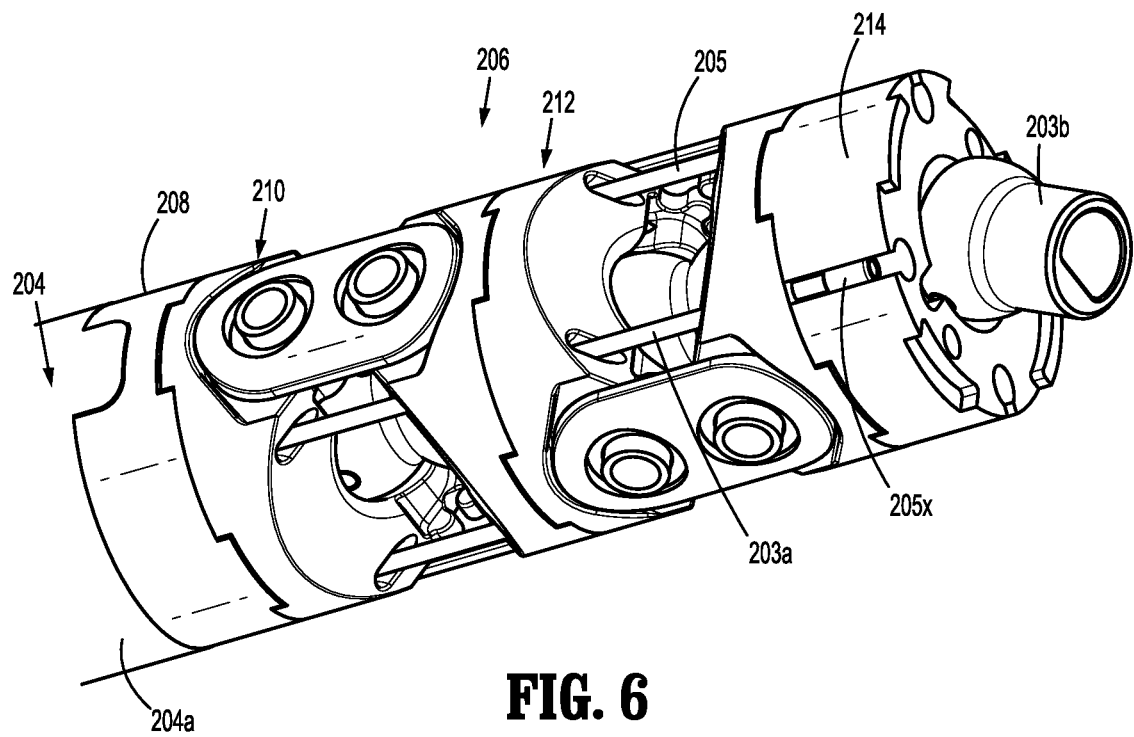

Turning to FIGS. 5 and 6, wrist assembly 206 of elongated shaft 204 of electromechanical surgical instrument 200 includes, from proximal to distal, a first interface 208 coupled to a distal portion of an outer tube 204a of elongated shaft 204, a first joint 210 coupled to a distal portion of first interface 208, a second joint 212 coupled to a distal portion of first joint 210 and angularly displaced therefrom (e.g., offset 90 degrees), and a second interface 214 coupled to a distal portion of second joint 212.

Figure 7:
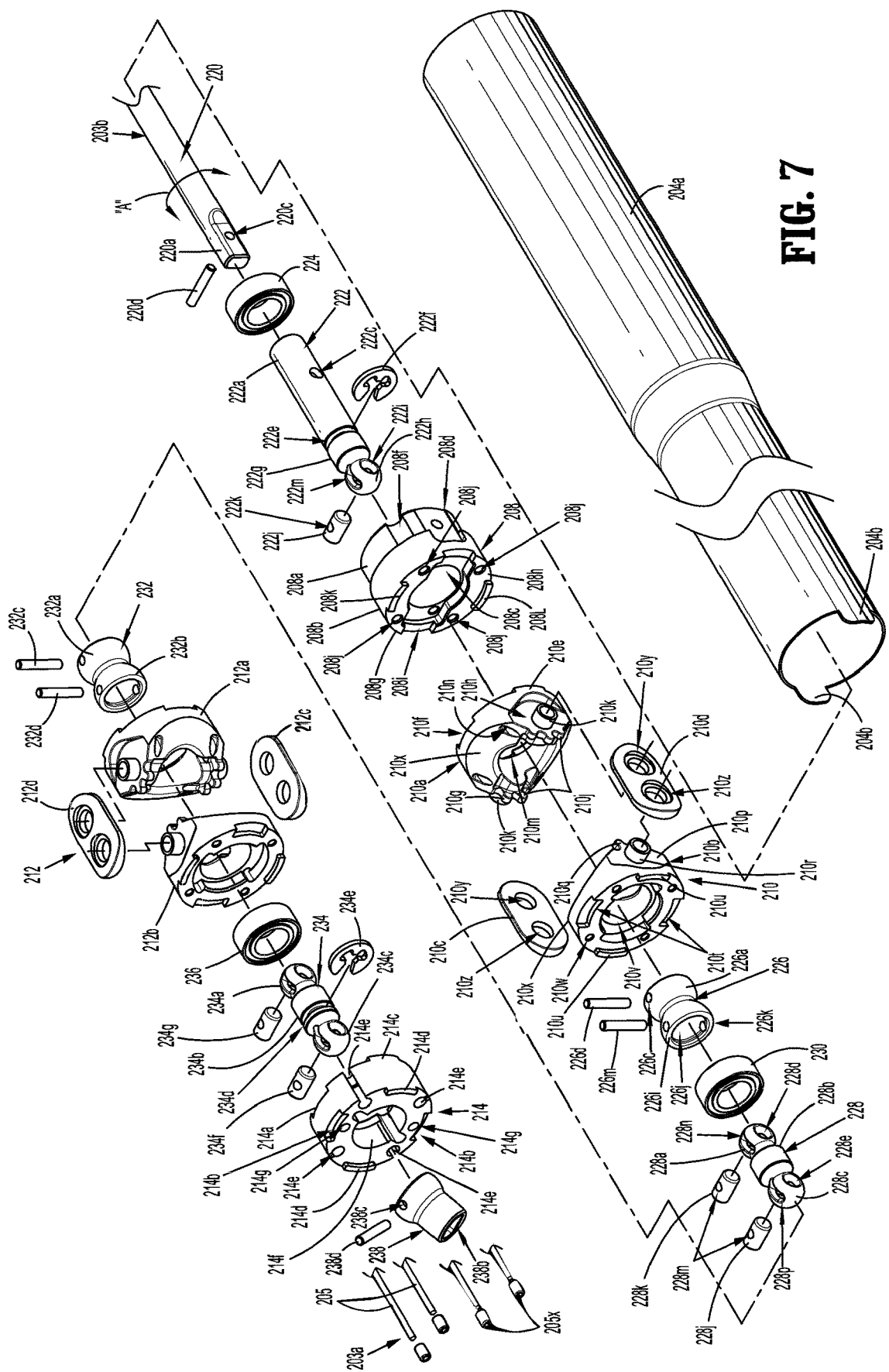
FIG. 7 is a perspective view, with parts separated, of the elongated shaft assembly of FIG. 4.
Figure 8:
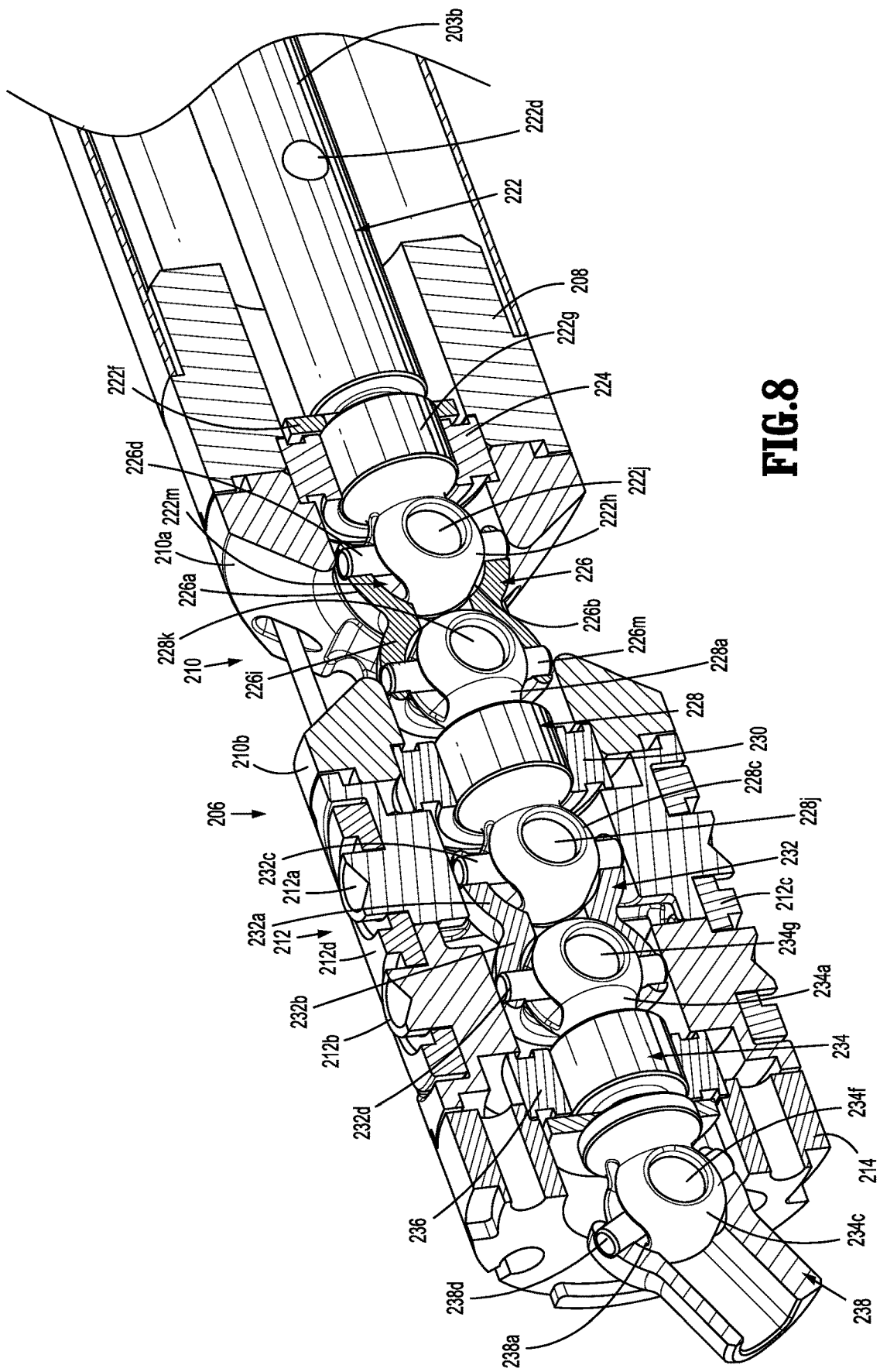
FIG. 8 is an enlarged, cross-sectional view of the wrist assembly of FIG. 5 as taken along section line 8-8 of FIG. 5

With reference to FIG. 7, first interface 208 of wrist assembly 206 is in the form of a tubular interface and includes a proximal housing 208a and a distal housing 208b that extends distally from proximal housing 208a, and a central opening 208c that is defined therethrough to receive firing assembly 203b of drive assembly 203. Proximal housing 208a of first interface 208 defines a pair of side slots 208d (only one side slot 208d shown with the other identically disposed on the opposite side of proximal housing 208a) that receive distally extending tabs 204b of outer tube 204a. Proximal housing 208a further defines a plurality of cable channels 208f (e.g., four) disposed at circumferentially spaced apart locations about proximal housing 208a (only one cable channel 208f is explicitly shown). Distal housing 208b defines a first ledge 208g and a second ledge 208h that define a transverse channel 208i between the first and second ledges 208g, 208h. First and second ledges 208g, 208h define cable apertures 208j (e.g., two each) that align with cable channels 208f to receive cables 205 of cable drive assembly 203a of drive assembly 203 therethrough. First and second ledges 208g, 208h further include distal tabs 208k, 208L that extend distally therefrom.

Figure 9:
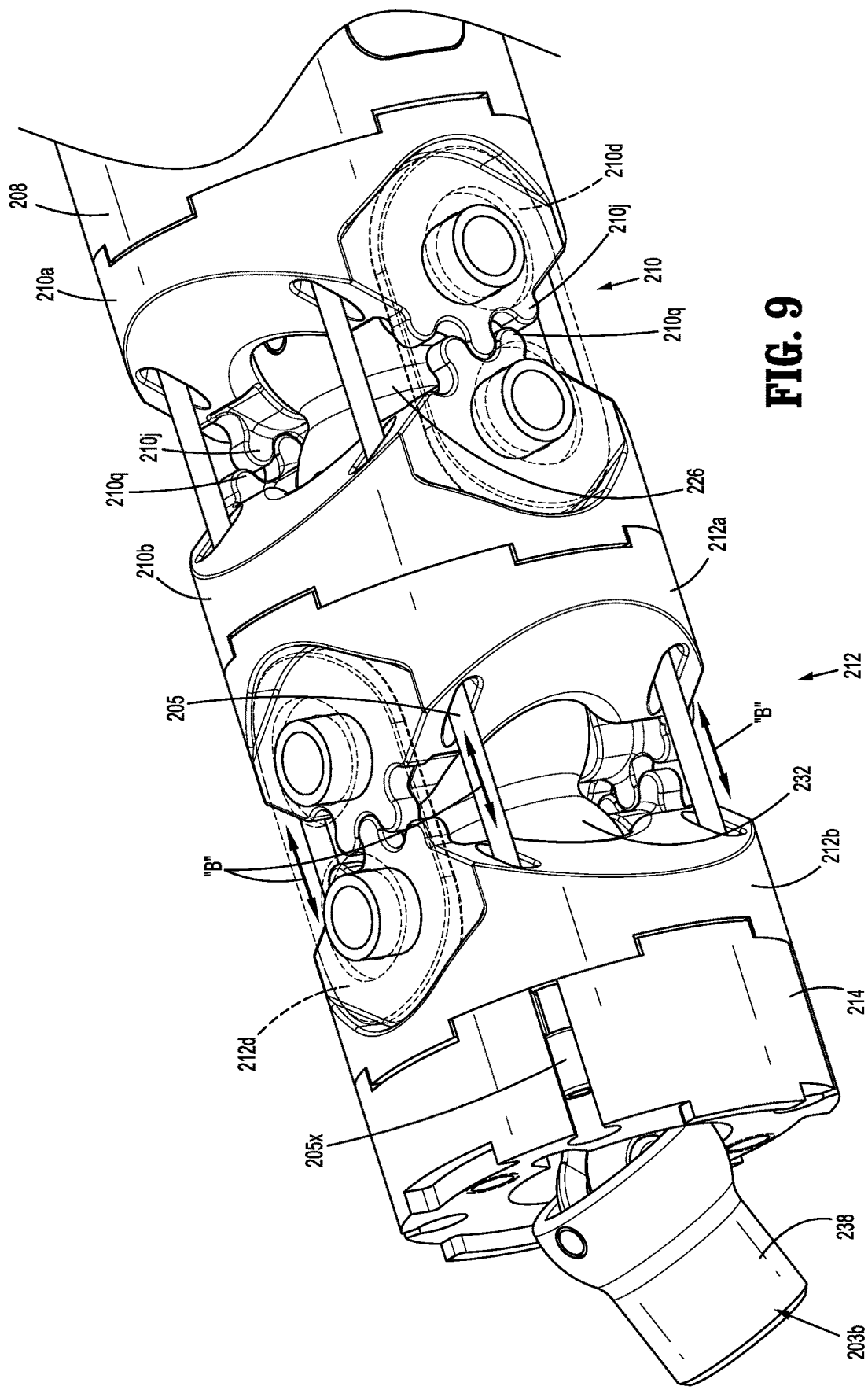
FIG. 9 is an enlarged view of the wrist assembly of FIG. 5 with portions thereof shown in phantom for clarity.

First joint 210 of wrist assembly 206 includes a proximal segment 210a and a distal segment 210b that are pivotally coupled together by links or caps 210c, 210d that help resist axial loading (created by tensile forces from cables 205) and misalignment in a transverse direction. In addition, links 210c, 210d help maintain clearance of, for instance, enmeshed gear teeth (see, e.g., FIG. 9 illustrating link 210d maintaining sufficient distance or axial separation between gear teeth 210j and 210q so that gear teeth 210j and 210q do not bind).

Proximal segment 210a of first joint 210 includes proximal tabs 210e (only one shown with an identical tab 210e shown on an opposite side of proximal segment 210a) that are received within transverse channel 208i of first interface 208. Proximal segment 210a defines a transverse recess 210f that is angularly displaced from proximal tabs 210e (e.g., 90 degrees) and positioned to receive distal tabs 208k, 208L of first interface 208 to prevent proximal segment 210a of first joint 210 from rotating relative to first interface 208 about longitudinal axis "L-L" (FIG. 2) (e.g., tongue and groove type interconnection). Proximal segment 210a includes a first coupler or gear 210g and a second coupler or gear 210h that extend distally from proximal segment 210a on opposed sides of proximal segment 210a. First and second gears 210g, 210h have a plurality of spaced apart teeth 210j. First and second gears 210g, 210h include pins 210k that extend laterally (e.g., perpendicularly) therefrom for engagement with links 210d, 210c of first joint 210. Any of the presently disclosed pins may include rivets or the like. Gears 210h, 210g are recessed from side surfaces of proximal segment 210a of first joint 210 to facilitate movement of links 210c, 210d of first joint 210 and distal segment 210b of first joint 210 relative to proximal segment 210a, as distal segment 210b articulates relative to proximal segment 210a. Proximal segment 210a of first joint 210 further defines a central opening 210m for receiving firing assembly 203b of drive assembly 203 therethrough, and a plurality of cable apertures 210n (e.g., four) for receiving the cables 205 of cable drive assembly 203a of drive assembly 203 therethrough.

Distal segment 210b of first joint 210 includes a coupler with knuckles or gears 210p (only one shown with a second identical coupler or gear 210p shown on an opposite side of distal segment 210b) that extend proximally from distal segment 210b and are positioned to enmesh or geometrically interlock (e.g., teeth 210q thereof) with first and second gears 210g, 210h of proximal segment 210a of first joint 210 to maintain rolling contact between respective interlocked gears (e.g., 210p, 210h; see FIGS. 7, 9 and 13) and to prevent an 'S' condition in the joint where the end effector location would be non-deterministic. Distal segment 210b further includes pins or bosses 210r (only one shown with a second identical pin 210r shown on an opposite side of distal segment 210b) that extend laterally from (e.g., perpendicularly from) gears 210p. Distal segment 210b further defines recesses 210t and includes distally extending tabs 210u that are alternately interspersed and disposed at angularly displaced locations (e.g., 90 degrees apart) about a distal end portion of distal end segment 210b. Distal segment 210b defines a central opening 210v for receiving firing assembly 203b therethrough and a plurality of cable apertures 210w (e.g., four) for receiving cables 205 of cable drive assembly 203a therethrough.

Each of proximal and distal segments 210a, 210b of first joint 210 include a pair of tapered surfaces 210x that provide space between the distal and proximal segments 210a, 210b of first joint 210 to enable distal segment 210b to articulate relative to proximal segment 210a as teeth 210j, 210q of proximal and distal segments 210a, 210b enmesh with one another. Tapered surfaces 210x of proximal segment 210a are configured to contact tapered surfaces of distal segment 210b to limit articulation (e.g., define maximum articulation in a given direction) of distal segment 210b relative to proximal segment 210a.

Links 210c, 210d of first joint 210 define proximal and distal pin apertures 210y, 210z that receive pins 210k, 210r of proximal and distal segments 210a, 210b, respectively, to secure proximal and distal segments 210a, 210b of first joint 210 together and enable distal segment 210b to articulate relative to proximal segment 210a.

Second joint 212 of wrist assembly 206 is identical to first joint 210 of wrist assembly 206 but is angularly displaced (e.g., 90 degrees) relative to first joint 210 so that first and second joints 210, 212 can interconnect and articulate/pivot relative to one another. In particular, second joint 212 includes a proximal segment 212a and a distal segment 212b that are pivotally coupled together by links 212c, 212d such that proximal segment 212a, distal segment 212b, and links 212c, 212d of second joint 212 are identical to proximal segment 210a, distal segment 210b, and links 210c, 210d of first joint 210, respectively. Proximal segment 212a of second joint 212 is coupled to distal segment 210b of first joint 210 such that proximal segment 212a of second joint 212 is rotationally locked to distal segment 210b of first joint 210 (e.g., tongue and groove type interconnection). In this manner, proximal and distal segments 212a, 212b of second joint 212 can articulate/pivot relative to one another while distal segment 210b of first joint 210 articulates/pivots relative to proximal segment 210a of first joint 210.

Second interface 214 of wrist assembly 206 is in the form of a tubular interface and defines proximal and distal recesses 214a, 214b that correspond to, and/or are aligned with, one another, respectively. Second interface 214 includes proximal and distal tabs 214c, 214d that correspond to, and/or are aligned with, one another, respectively. Proximal recesses 214a and proximal tabs 214c of second interface 214 are configured to engage distally extending tabs 210u and recesses 210t of second joint 212 (e.g., tongue and groove type connection) to rotationally lock second interface 214 to distal segment 212b of second joint 212. Second interface 214 further defines cable slots 214e at circumferentially spaced apart locations about second interface 214 that are positioned to receive ferrules 205x and cables 205 therein to secure cables 205 to second interface 214. Second interface 214 further defines a central opening 214f that is configured to receive firing assembly 203b of drive assembly 203 therethrough. Second interface 214 also defines alignment holes 214g to facilitate alignment and securement of wrist assembly 206 to end effector 300 of electromechanical surgical instrument 200.

With reference to FIGS. 7-14, firing assembly 203b of drive assembly 203 of electromechanical surgical instrument 200, which is in the form of a multi-stage universal joint assembly, includes a drive shaft 220, a ball shaft 222 that extends distally from drive shaft 220, a first bearing 224 supported on ball shaft 222 to rotatably support ball shaft 222, a first ball housing 226 coupled to a distal portion of ball shaft 222, a first dual ball shaft 228 coupled to first ball housing 226 and rotatably supported by a second bearing 230, a second ball housing 232 coupled to a distal portion of first dual ball shaft 228, a second dual ball shaft 234 coupled to a distal portion of second ball housing 232 and rotatable supported by a third bearing 236, and a drive coupler 238 supported on a distal portion of second dual ball shaft 234.

Drive shaft 220 of firing assembly 203b of drive assembly 203 has a proximal end portion coupled to a driven member 211 (FIG. 15) of drive assembly 203 that operably couples to one or more of motors 50 of robotic surgical assembly 100 (see FIGS. 1 and 15) to enable drive shaft 220 to rotate about longitudinal axis "L-L," as indicated by arrows "A" (FIG. 7). Drive shaft 220 extends to a keyed distal portion 220a configured to be received by a proximal portion of ball shaft 222. Keyed distal portion 220a is shown with a rectangular configuration, but may have any suitable non-circular configuration such as a triangle, square, star, etc. Keyed distal portion 220a defines a pin hole 220c configured to receive a pin 220d therein.

Ball shaft 222 of firing assembly 203b has proximal portion 222a defining a keyed bore 222b (FIG. 10) that is configured to receive keyed distal portion 220a of drive shaft 220 therein to enable ball shaft 222 to rotate with drive shaft 220. Keyed bore 222b can have any suitable non-circular configuration and may be configured to complement keyed distal portion 220a of drive shaft 220 to facilitate a rotatably locked connection between ball shaft 222 and drive shaft 220 such that ball shaft 222 and drive shaft 220 rotate together. Ball shaft 222 further defines a pin hole 222c that receives pin 220d therein to rotatably couple drive shaft 220 to ball shaft 222 (see FIGS. 7 and 11). Ball shaft 222 defines an annular clip channel 222e in an outer surface thereof. Annular clip channel 222e is configured to receive a clip 222f (e.g., an E-clip) to obstruct axial movement of first bearing 224 to enable first bearing 224 of firing assembly 203b to be maintained axially fixed on a bearing surface 222g of ball shaft 222. Ball shaft 222 further includes a ball member 222h supported on a distal end portion of ball shaft 222. Ball member 222h of ball shaft 222 defines a transverse opening 222i therethrough configured to receive a ball pin 222j defining a pin hole 222k therein. Ball member 222h further defines an elongated slot 222m that is configured to align with pin hole 222k of ball pin 222j.

First ball housing 226 of firing assembly 203b of drive assembly 203 has a proximal shell 226a defining a proximal bore 226b therein that rotatably receives ball member 222h of ball shaft 222 therein. Proximal shell 226a further defines a pin passage 226c that receives a pin 226d therethrough. Pin 226d is receivable within elongated slot 222m of ball member 222h of ball shaft 222 while received through proximal shell 226a of first ball housing 226 to rotatably couple ball member 222h of ball shaft 222 to proximal shell 226a of first ball housing 226 (see FIGS. 7 and 8) to define a universal joint and to enable pin 226d to move through elongated slot 222m of ball member 222h as first ball housing 226 articulates/pivots about ball member 222h (see, for example, articulation/pivoting indicated by arrows "D" in FIG. 16).

First ball housing 226 of firing assembly 203b also includes a distal shell 226i configured to couple to first dual ball shaft 228. Distal shell 226i defines a distal bore 226j and a pin passage 226k therethrough that receives a pin 226m therein to rotatably/articulatably couple first dual ball shaft 228 to distal shell 226i (e.g., to define another universal joint).

First dual ball shaft 228 of firing assembly 203b includes a proximal ball member 228a that extends proximally from a bearing support surface 228b, and a distal ball member 228c that extends distally from bearing support surface 228b that rotatably supports second bearing 230. Proximal and distal ball members 228a, 228c define transverse openings 228d, 228e therethrough, respectively, and elongated slots 228n, 228p therethrough, respectively. Transverse openings 228d, 228e of proximal and distal ball members 228a, 228c are configured to receive ball pins 228j, 228k therein, respectively. Each ball pin 228j, 228k defines a pin hole 228m therein. Pin hole 228m of ball pin 228k and elongated slot 228n of ball member 228a are configured to receive pin 226m of first ball housing 226 to rotatably/articulatably couple first dual ball shaft 228 to distal shell 226i of first ball housing 226 (e.g., to define universal joints).

Second ball housing 232 of firing assembly 203b of drive assembly 203 is identical to first ball housing 226 of firing assembly 203b and includes a proximal shell 232a, a distal shell 232b that extends distally from proximal shell 232a, and pins 232c, 232d that are received within proximal and distal shells 232a, 232b, respectively. Pins 232c, 232d of second ball housing 232 rotatably couple second ball housing 232 to ball members 228c, 234a of first dual ball shaft 228 and second dual ball shaft 234, respectively, (e.g., to define universal joints) similar to the rotatable/articulatable coupling described above with respect to first ball housing 226 and ball members 222h, 228a of ball shaft 222 and first dual ball shaft 228, respectively.

Second dual ball shaft 234 of firing assembly 203b of drive assembly 203 is similar to first dual ball shaft 228 of firing assembly 203b and includes a proximal ball member 234a that extends proximally from a bearing support surface 234b that supports third bearing 236, and a distal ball member 234c that extends distally from bearing support surface 234b. Bearing support surface 234b further defines an annular clip channel 234d that is configured to receive a clip 234e (e.g., an E-clip) to obstruct axial movement of third bearing 236 and axially support third bearing 236 on bearing support surface 234b of second dual ball shaft 234. Second dual ball shaft 234 further includes ball pins 234f, 234g. Proximal ball member 234a of second dual ball shaft 234 is rotatably coupled to distal shell 232b of second ball housing 232 (e.g., a universal joint) and distal ball member 234c of second dual ball shaft 234 rotatably supports drive coupler 238 thereon.

Drive coupler 238 of firing assembly 203b defines a proximal bore 238a (FIG. 8) that rotatably receives distal ball member 234c of second dual ball shaft 234, and a distal bore 238b that is configured to couple to end effector 300 of electromechanical surgical instrument 200. Although distal bore 238b of drive coupler 238 is shown including a non-circular configuration, such as a D-shaped configuration, distal bore 238b can have any non-circular configuration (e.g., triangular, rectangular, pentagonal, etc.) to facilitate a rotatably locked connection between firing assembly 203b and end effector 300 so that end effector 300, or components thereof, can rotate with firing assembly 203b of drive assembly 203. Drive coupler 238 further defines a pin hole 238c that receives a pin 238d to rotatably couple drive coupler 238 to distal ball member 234c of second dual ball shaft 234.

With reference to FIG. 3, end effector 300 of electromechanical surgical instrument 200 includes a mounting portion 302 on a proximal end portion thereof, and a first jaw member 304 (e.g., an anvil) and a second jaw member 306 (e.g., a cartridge assembly) that are coupled to mounting portion 302. First and second jaw members 304, 306 are positioned for pivotal movement between open (FIG. 3) and closed (not shown) positions. First and second jaw members 304, 306 support a drive assembly 308 that is configured to fire a fastener cartridge 310 supported in second jaw member 306.

As seen in FIG. 4, mounting portion 302 of end effector 300 includes mounting tabs 302a and defines mounting recesses 302b that engage respective distal recesses 214b and distal tabs 214d of second interface 214 of wrist assembly 206. Mounting portion 302 further includes alignment pins 302c that are received within alignment holes 214g of second interface 214 of wrist assembly 206. Mounting portion 302 further defines a central opening 302d that is configured to receive drive coupler 238 of firing assembly 203b to couple drive coupler 238 to drive assembly 308 of end effector 300.

Figure 10:
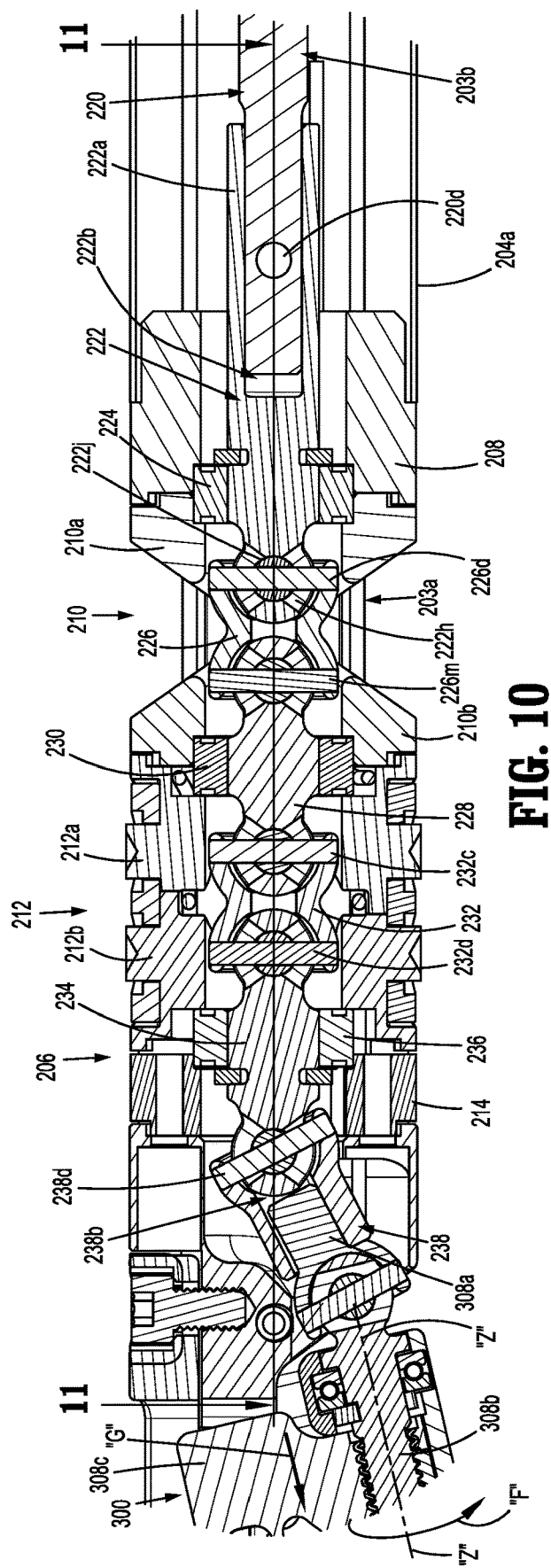
FIG. 10 is an enlarged, longitudinal, cross-sectional view of the indicated area of detail shown in FIG. 2.
Figure 11:
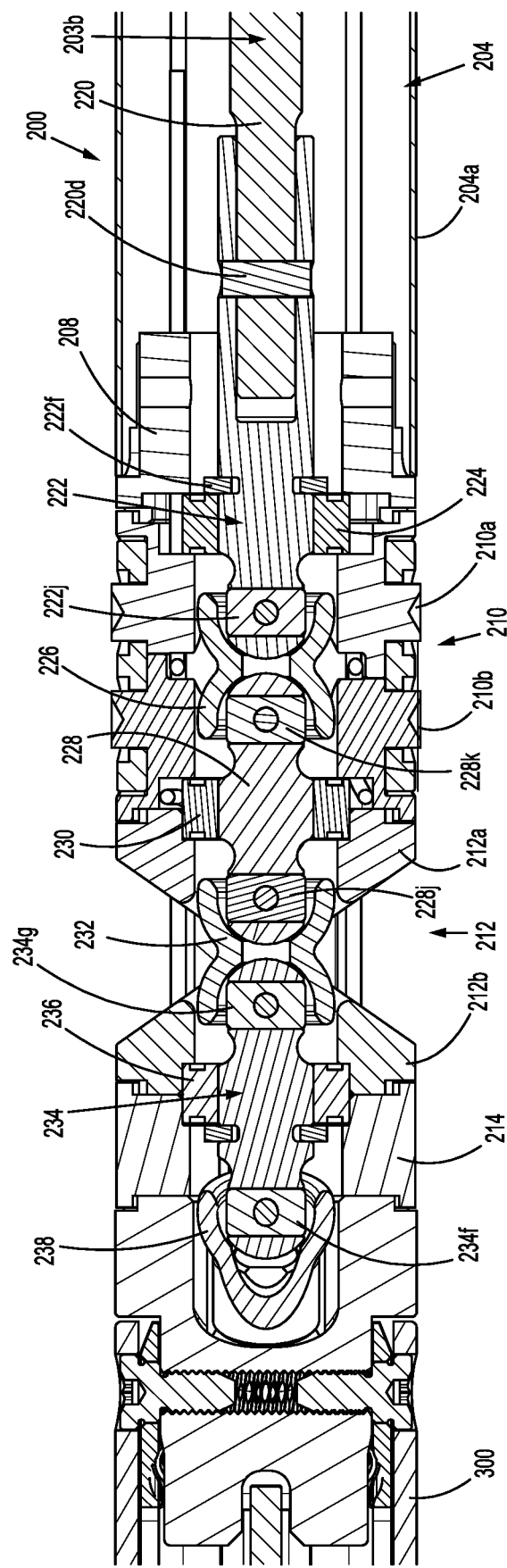
FIG. 11 is a cross-sectional view of the wrist assembly of FIG. 5 as taken along the section line 11-11 of FIG. 10.
Figure 14:
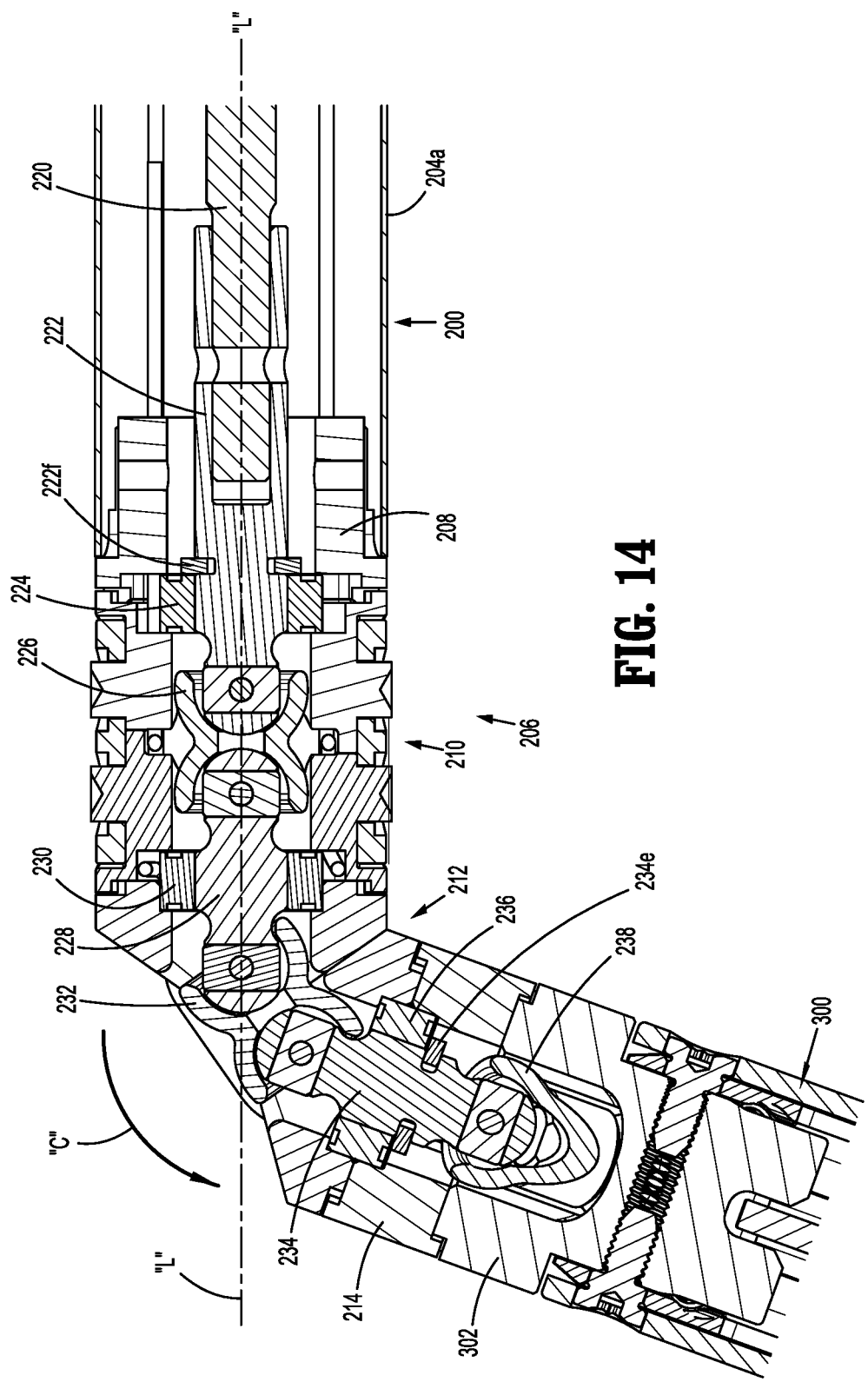
FIG. 14 is a longitudinal, cross-sectional view of FIG. 13.

With reference to FIG. 10, drive assembly 308 of end effector 300 includes a driven coupler 308a that is received in distal bore 238b of drive coupler 238 of firing assembly 203b of drive assembly 203. Driven coupler 308a of drive assembly 308 includes a non-circular configuration (e.g., D-shape) that is keyed to distal bore 238b of drive coupler 238 of firing assembly 203b so that driven coupler 308a and drive coupler 238 are rotatably locked with respect to one another such that driven coupler 308a and drive coupler 238 rotate together as drive coupler 238 rotates. Driven coupler 308a is pinned to a lead screw 308b that supports a drive beam 308c such that rotation of driven coupler 308a causes lead screw 308b to rotate and axially advance drive beam 308c along lead screw 308b. For a more detailed description of components of example end effectors similar to end effector 300, reference can be made to U.S. Patent Application Publication Nos. 2016/0242779 and 2015/0297199, the entire disclosures of each of which are incorporated by reference herein.

Figure 16:
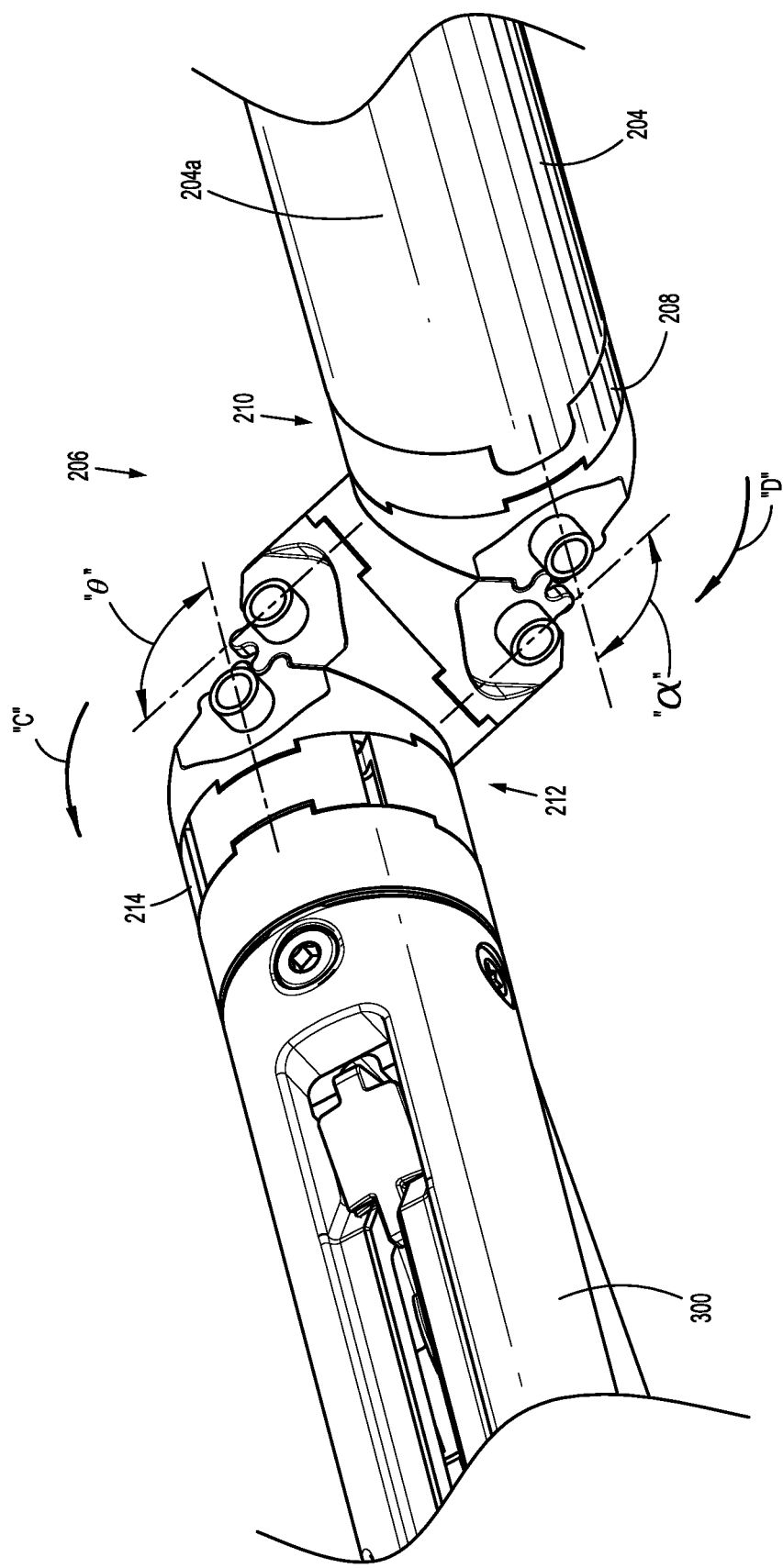
FIG. 16 is an enlarged view of the indicated area of detail shown in FIG. 15 with portions thereof removed for clarity.

In use, with electromechanical surgical instrument 200 coupled to robotic surgical assembly 100 as seen in FIG. 1, one or more motors 50 of instrument drive unit 110 can be actuated to rotate one or more of driven members 209 of electrosurgical instrument 200 to push and/or pull one or more cables 205 of cable drive assembly 203a of drive assembly 203 of electromechanical surgical instrument 200. As cables 205 of cable drive assembly 203a axially translate, as indicated by arrows "B" (FIG. 9), one or both of first and second joints 210, 212 of wrist assembly 206 rotate and/or articulate with one or more of first ball housing 226, first dual ball shaft 228, second ball housing 232, and/or second dual ball shaft 234 of firing assembly 203b of drive assembly 203, relative to longitudinal axis "L-L," as indicated by arrows "C" and "D" (see FIGS. 12-16). Each of first and second joints 210, 212 can be configured to articulate through an articulation angle of up to 70 degrees such that first joint 210 can be articulated through an articulation angle "α" up to 70 degrees while second joint 212 is articulated through an articulation angle "Θ" up to 70 degrees, as seen in FIG. 16. As can be appreciated, one or more components of firing assembly 203b (e.g., first ball housing 226, first dual ball shaft 228, second ball housing 232, and/or second dual ball shaft 234, etc.) pivot, rotate, and/or articulate as first and second joint 210, 212 pivot, rotate, and/or articulate.

While first and/or second joints 210, 212 of wrist assembly 206 are disposed in an articulated (FIGS. 12-16) or an unarticulated position (FIG. 2), firing assembly 203b can be rotated about longitudinal axis "L-L," as indicated by arrows "A," (see FIGS. 2 and 7) in response to rotation of driven member 211 (FIG. 15) by one or more of motors 50 of instrument drive unit 110 (FIG. 1). Rotation of firing assembly 203b of drive assembly 203 causes drive coupler 238 of firing assembly 203b to rotate lead screw 308b of end effector 300 about its axis, e.g., axis "Z-Z," as indicated by arrows "F" (FIG. 10). Rotation of lead screw 308b of end effector 300 causes drive beam 308c of end effector 300 to advance distally along lead screw 308b, as indicated by arrow "G," so that first and second jaw members 304, 306 of end effector 300 move from the open or unapproximated position (FIG. 3) thereof to the closed or approximated position (not shown) thereof. As drive beam 308c of end effector 300 continues to advance distally along first and second jaw members 304, 306, drive beam 308c fires fastener cartridge 310 (FIG. 3) to fasten and/or sever tissue captured between first and second jaw members 304, 306 similar to that described in U.S. Patent Application Publication No. 2015/0297199 referenced above.

Although electromechanical surgical instrument 200 is described herein in connection with robotic surgical system 1, the presently disclosed electromechanical surgical instruments 200 can be provided in the form of a hand held electromechanical instrument, which may be manually driven and/or powered. For instance, U.S. Patent Application Publication No. 2015/0297199, referenced above, describes one example of a powered hand held electromechanical instrument, one or more of the components of which (e.g., the surgical device or handle thereof) can be utilized in connection with the presently disclosed surgical instrument 200.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A robotic electromechanical surgical instrument, comprising:
   a housing;
   an elongated shaft defining a longitudinal axis and extending distally from the housing;
   a wrist assembly supported on the elongated shaft;
   a rotatable drive shaft extending through the elongated shaft and through at least a portion of the wrist assembly;
   an end effector coupled to the wrist assembly, the end effector including a lead screw rotatably supported therein;
   a universal joint assembly supported within the wrist assembly and operatively interconnecting the rotatable drive shaft and the lead screw, the universal joint assembly being rotatable by the rotatable drive shaft to actuate a function of the end effector; and
   a plurality cables coupled to the wrist assembly, the plurality of cables movable to manipulate the wrist assembly to articulate the end effector relative to the longitudinal axis.

2. The robotic electromechanical surgical instrument of claim 1, wherein the wrist assembly includes a first joint coupled to a second joint; and wherein the plurality of cables are movable to manipulate the first joint and the second joint to enable the universal joint assembly and the wrist assembly to articulate relative to the longitudinal axis.

3. The robotic electromechanical surgical instrument of claim 2, wherein the first and second joints are angularly displaced relative to one another about the longitudinal axis.

4. The robotic electromechanical surgical instrument of claim 2, wherein each of the first and second joints has a proximal segment and a distal segment, the proximal and distal segments supported for movement relative to one another to facilitate articulation of the wrist assembly relative to the longitudinal axis of the elongated shaft.

5. The robotic electromechanical surgical instrument of claim 4, wherein the proximal and distal segments of the first joint include couplers supported in rolling contact with one another.

6. The robotic electromechanical surgical instrument of claim 5, wherein the proximal and distal segments of the second joint include couplers supported in rolling contact with one another.

7. The robotic electromechanical surgical instrument of claim 4, wherein the proximal and distal segments of the first joint are coupled together by a first pair of links, and wherein the proximal and distal segments of the second joint are coupled together by a second pair of links.

8. The robotic electromechanical surgical instrument of claim 2, wherein the first joint of the wrist assembly is coupled to the elongated shaft by a first tubular interface, and wherein the second joint of the wrist assembly is coupled to the end effector by a second tubular interface.

9. The robotic electromechanical surgical instrument of claim 8, wherein the first joint is rotationally locked to the first tubular interface, and wherein the second joint is rotationally locked to the second tubular interface.

10. The robotic electromechanical surgical instrument of claim 2, wherein the first and second joints define central openings therethrough that are positioned to receive the universal joint assembly therein.

11. The robotic electromechanical surgical instrument of claim 2, wherein the universal joint assembly includes a plurality of universal joints with at least two universal joints of the plurality of universal joints positioned at longitudinally spaced apart locations along the universal joint assembly.

12. A robotic surgical system, comprising:
a robotic surgical assembly; and
an electromechanical surgical instrument selectively mounted to the robotic surgical assembly, the surgical instrument including:
a housing;
an elongated shaft defining a longitudinal axis and extending distally from the housing;
a wrist assembly supported on the elongated shaft;
a rotatable drive shaft extending through the elongated shaft and through at least a portion of the wrist assembly;
an end effector coupled to the wrist assembly, the end effector including a lead screw rotatably supported therein;
a universal joint assembly supported within the wrist assembly and operatively interconnecting the rotatable drive shaft and the lead screw, the universal joint assembly being rotatable by the rotatable drive shaft to actuate a function of the end effector; and
a plurality cables coupled to the wrist assembly, the plurality of cables movable to manipulate the wrist assembly to articulate the end effector relative to the longitudinal axis.

13. The robotic surgical system of claim 12, wherein the wrist assembly includes a first joint coupled to a second joint; and wherein the plurality of cables are movable to manipulate the first joint and the second joint to enable the universal joint assembly and the wrist assembly to articulate relative to the longitudinal axis.

14. The robotic surgical system of claim 13, wherein the first and second joints are angularly displaced relative to one another about the longitudinal axis.

15. The robotic surgical system of claim 13, wherein each of the first and second joints has a proximal segment and a distal segment, the proximal and distal segments supported for movement relative to one another to facilitate articulation of the wrist assembly relative to the longitudinal axis of the elongated shaft.

16. The robotic surgical system of claim 15, wherein the proximal and distal segments of the first joint include couplers supported in rolling contact with one another.

17. The robotic surgical system of claim 16, wherein the proximal and distal segments of the second joint include couplers supported in rolling contact with one another.

18. The robotic surgical system of claim 15, wherein the proximal and distal segments of the first joint are coupled together by a first pair of links, and wherein the proximal and distal segments of the second joint are coupled together by a second pair of links.

19. The robotic surgical system of claim 13, wherein the first joint of the wrist assembly is coupled to the elongated shaft by a first tubular interface, and wherein the second joint of the wrist assembly is coupled to the end effector by a second tubular interface.

20. The robotic surgical system of claim 19, wherein the first joint is rotationally locked to the first tubular interface, and wherein the second joint is rotationally locked to the second tubular interface.

21. The robotic surgical system of claim 13, wherein the first and second joints define central openings therethrough that are positioned to receive the firing assembly therein.

22. The robotic surgical system of claim 13, wherein at least two universal joints of the plurality of universal joints are positioned at longitudinally spaced apart locations along the firing assembly.

* * * * *